US006352706B1

(12) United States Patent
Puritch

(10) Patent No.: US 6,352,706 B1
(45) Date of Patent: Mar. 5, 2002

(54) NATURALLY OCCURRING ENHANCER OF METAL TOXICANTS IN MOLLUSCS

(75) Inventor: George S. Puritch, Saanichton (CA)

(73) Assignee: W. Neudorff GmbH KG (DE)

(*) Notice: Subject to any disclaimer, the term of this patent is extended or adjusted under 35 U.S.C. 154(b) by 0 days.

(21) Appl. No.: 09/241,686

(22) Filed: Feb. 1, 1999

Related U.S. Application Data

(60) Provisional application No. 60/073,827, filed on Feb. 5, 1998.

(51) Int. Cl.$^7$ ........................... A01N 25/10; A01N 37/44
(52) U.S. Cl. ..................... 424/410; 424/405; 424/407; 424/604; 424/630; 424/631; 424/632; 424/638; 424/641; 424/646; 424/685; 514/494; 514/499; 514/500; 514/502; 514/566; 514/574
(58) Field of Search .......................... 424/405, 407, 424/408–410, 604, 630–632, 638, 641, 643, 646–648, 685; 514/494, 499, 500, 502, 566, 574

(56) References Cited

U.S. PATENT DOCUMENTS

| | | | |
|---|---|---|---|
| 2,836,537 A | 5/1958 | Skaptason et al. ............ 167/22 |
| 4,704,233 A | 11/1987 | Hartman et al. ............ 252/527 |
| 4,765,979 A | 8/1988 | Nielson ........................ 424/84 |
| 5,017,620 A | * 5/1991 | Grassman et al. ........... 574/698 |
| 5,162,349 A | 11/1992 | Beriger et al. ............... 514/363 |
| 5,362,749 A | 11/1994 | Henderson et al. ......... 514/492 |
| 5,437,870 A | 8/1995 | Puritch et al. .............. 424/408 |
| 5,554,791 A | 9/1996 | Lin et al. .................... 562/565 |
| 5,733,858 A | 3/1998 | Wilson et al. ............... 510/361 |
| 5,874,262 A | 2/1999 | Zähner et al. ............... 435/128 |

FOREIGN PATENT DOCUMENTS

| | | | |
|---|---|---|---|
| AU | 81174/91 | 6/1992 | |
| AU | PN7757 | 1/1996 | |
| AU | PO1708 | 8/1996 | |
| AU | 12203/97 | 1/1997 | |
| AU | 1220397 | 7/1997 | |
| AU | 7742098 | 9/1998 | |
| AU | 4107899 | 2/2000 | ........ A01N/55/02 |
| GB | 2207866 | 2/1989 | |
| JP | 76112481 | 9/1976 | ........ A01N/9/22 |
| WO | WO 89/01287 | 2/1989 | |
| WO | 8901287 | 2/1989 | ........ A01N/35/02 |
| WO | WO 96/05728 | 2/1996 | |
| WO | 9605728 | 2/1996 | ........ A01N/25/00 |
| WO | 9726789 | 7/1997 | ........ A01N/37/44 |
| WO | 9925194 | 5/1999 | ........ A01N/55/02 |
| WO | 0008933 | 2/2000 | ........ A01N/55/02 |

OTHER PUBLICATIONS

Bullock, J. et al., "Contact Uptake of Metal Compounds and Their Molluscicidal Effect on the Field Slug, *Deroceras reticulatum* (Müller) (Pulmonata: Limacidae)," *Crop Protection*, vol. 11, 329–334 (Aug. 1992).

Henderson, I. et al., *Ann. Appl. Biol.*, vol. 116, 273–8 (1990).
Henderson, I. et al., *Aspects of Appl. Biol.*, vol. 13, 341–7 (1986).
Henderson, I. et al., *Crop Protection*, vol. 9, 131–4 (Apr. 1990).
Henderson, I. et al., 1989 BCPC Mono. No. 41 Slugs and Snails in World Agriculture, 289–94 (1989).
Nishikiori, T. et al., "Production by Actinomycetes of (S,S)–N,N'–Ethylenediamine–Disuccinic Acid, an Inhibitor of Phospholipase C," *The Journal of Antibiotics*, 426–7 (Apr. 1984).
Schowanek, D. et al., "Biodegradation of [S,S], [R,R] and Mixed Stereoisomers of Ethylene Diamine Disuccinic Acid (EDDS), a Transition Metal Chelator," *Chemoshpere*, vol. 34, No. 11, 2375–91 (1997).
Anderegg, G., "Complexones," in "Comprehensive Co–Ordination Chemistry," 1$^{st}$ Edition, Wilkinson, G. Oxford Pergamon Press, Chapter 20.3; 777–792 (1987).
AVA Information Sheet, Issue No. 6; 1–3 (Released Jun. 11, 1997).
Clark, S.J., et al., "Metal Chelate Molluscicides: The Redistribution of Iron Diazaalkanolates from the Gut Lumen of the Slug, *Deroceras reticulatum* (Müller) (Pulmonata: Limacidae)," *Pestic. Sci.*, vol. 44; 381–388 (1995).
Gustafson, R.L., et al., "Hydrolic Tendencies of Ferric Chelates," *J. Phys. Chem.*, vol. 67; 576–581 (Mar. 1963).
Henderson, I.F., et al., "Control of Slugs with Contact–Action Molluscicides," *Ann. Appl. Biol.*, vol. 116; 273–278 (1990).
Henderson, I.F., et al., "Laboratory and Field Assessment of a New Aluminum Chelate Slug Poison," *Crop Protection*, vol. 9; 131–134 (Apr. 1990).
Henderson, I.F., et al., "A New Group of Molluscicidal Compounds," *BCPC Mono. No. 41 Slugs and Snails in World Agriculture*; 289–294 (1989).
Kari, F., et al., "Determination of the Reaction Quantum Yield for the Photochemical Degradation of Fe(III)–EDTA: Implications for the Environmental Fate of EDTA in Surface Waters," *Environ. Sci. Technol.*, vol. 29; 1008–1017 (1995).
Kelly, C.R., et al., "Can Different pH Environments in Slug Digestive Tracts be Exploited to Improve the Efficacy of Molluscicide Baits?," *Slug & Snail Pests in Agriculture*, BCPC Symposium Proceedings, No. 66; 83–90 (Sep. 24–26, 1996).
Marigomez, J.A., et al., "Feeding and Growth Responses to Copper, Zinc, Mercury and Lead in the Terrestrial Gastropod Arion After (Linne)," *J. Moll. Stud.*, vol. 52; 68–78 (1986).

(List continued on next page.)

*Primary Examiner*—Neil S. Levy
(74) *Attorney, Agent, or Firm*—Nutter McClennen & Fish LLP

(57) ABSTRACT

An ingestible mollusc poison contains a simple metal compound, an activity enhancing additive such as ethylene diamine disuccinic acid (EDDS) and derivatives thereof, and a carrier material edible to molluscs. In one embodiment the active agent of the mollusc poison may be in the form of a metal complex of EDDS. The composition may be used alone or in conjunction with molluscicidal co-active agents and/or fertilizers.

22 Claims, No Drawings

OTHER PUBLICATIONS

Material Safety Data Sheet for Multiguard, 1–3; updated Oct. 8, 1996.

Motekaitis, R.J., et al., New Multidentate Ligands. XXV. The Coordination Chemistry of Divalent Metal Ions with Diglycolic Acid, Carboxymethyltartronic Acid and Ditartronic Acid, *J. Coord. Chem.*, vol. 13; 265–271 (1984).

NRA Gazette and NRA Internet Data relating to Multicrop Snail and Slug Pellets, No. NRA 10; (Oct. 1, 1996).

Rico, M.I., et al., "Preparation of Fertilizers with Rosin and Tricalcium Phosphate Coated Zinc Chelates. Laboratory Characterization," *J. Agric. Food Chem.*, vol. 43; 2758–2761 (1995).

Schugar, H.J., et al., "Electrochemical and Spectral Studies of Dimeric Iron (III) Complexes," *J. Amer. Chem. Soc.*, vol. 90, No. 1; 71–77 (Jan. 1, 1969).

Schwarzenbach, G., et al., "Komplexone XVIII. Die Eisen(II)–und Eisen(III)–komplexe der Athylendiamintetraessigsäure und ihr Redoxgleichgewicht," *Helv. Chem. Acta.*, vol. 34, No. 65; 576–591 (1951).

Wilkins, R., et al., "The Kinetics of Monomer–Dimer Interconversion of Iron(III)–Ethylenediaminetetraacetate and Related Chelates," *Inorganic Chemistry*, vol. 8, No. 7; 1470–1473 (Jul. 1969).

Young, C., "Metal Chelates as Stomach Poison Molluscicides for Introduced Pests, *Helix Aspera, Theba Pisana, Cernuella Virgata* and *Deroceras Reticulatum* in Australia," *Slug & Snail Pests in Agriculture*, BCPC Symposium Proceedings, No. 66; 237–243 (Sep. 24–26 1996).

Aristarkhov, A.N., "Use of Microelement Fertilizer in Conditions of Intensive Chemical Treatment and Principles of Modeling for Determination of Requirements for Them," *Khim. Sel. Khoz.*, vol. 23(8), 15–22 (1985). [Abstract Only].

Henderson, I.F. and Martin, A.P., "Control of Slugs with Contact–Action Molluscicides," *Ann. Appl. Biol.*, vol. 116, 273–8 (1990).

Henderson, I.F. and Parker, K.A., "Problems in Developing Chemical Control of Slugs," *Aspects of Applied Biology*, vol. 13, 341–7 (1986).

Henderson, I.F. et al., "Laboratory and Field Assessment of a New Aluminium Chelate Slug Poison," *Crop Protection*, vol. 9, 131–4 (1990).

Henderson, I.F. et al., "A New Group of Molluscicidal Compounds," *1989 BCPC Mono. No. 41 Slugs and Snails in World Agriculture*, 289–94 (1989).

* cited by examiner

NATURALLY OCCURRING ENHANCER OF METAL TOXICANTS IN MOLLUSCS

CROSS-REFERENCE TO RELATED APPLICATIONS

This application is based on and claims priority from U.S. patent application Ser. No. 60/073,827, filed Feb. 5, 1998.

STATEMENT REGARDING FEDERALLY SPONSORED RESEARCH

Not applicable.

FIELD OF THE INVENTION

This invention relates to pest control compounds and, more particularly, to compositions effective to control pest molluscs by enhancing the effectiveness of metal poison absorption in molluscs.

BACKGROUND OF THE INVENTION

Terrestrial pulmonate gastropods such as slugs and snails are significant plant pests that affect commercial agriculture and horticulture and domestic gardens. These organisms are omnivorous and consume large amounts of vegetative material during their daily foraging. Consequently, they can seriously damage vegetable gardens and even plant crops during all phases of the growing cycle. Because of their destructive potential, control measures must be used to ensure adequate protection of the growing plants.

Aquatic molluscs, including the fresh water snails Bulinsu sp., Bulinus, Biomphalaria, and Oncomeania, and vectors of parasitic worms (e.g., Schistosoma), are also pests. Aquatic molluscs are controlled by a number of synthetic and botanical compounds.

Terrestrial pulmonate gastropods and aquatic molluscs are collectively referred to herein as "molluscs."

A wide variety of approaches have been used to combat pest molluscs. Perhaps the most common is the use of poisonous compounds called molluscicides. Molluscicides encompass a diverse group of chemical compounds including table salt (NaCl), calcium arsenate, copper sulfate and metaldehyde. Molluscicides, depending upon their mode of action, fall into two major groups: (1) contact poisons or (2) ingested poisons. As a contact poison, the molluscicides must come into physical contact with the exterior of the mollusc, either by external application or as a result of the mollusc traversing the bait on the ground. The poison is picked up by the proteinaceous slime coat of the mollusc and builds up in the mollusc's body until it reaches lethal proportions. One of the major drawbacks of contact-type molluscicides is that they have little effect if the molluscs are not physically touched by the chemical. Slugs or snails will be unaffected if they are hidden or migrate into an area after application of a contact molluscicide.

One of the few compounds that acts as both a contact and ingested poison is metaldehyde. This compound is commonly used as a long lasting bait, attracting the molluscs and killing them after ingestion of the compound. Despite its high effectiveness and its commercial popularity, metaldehyde is toxic to higher mammals and is a major contributor to domestic animal poisoning in the U.S. and Europe.

Heavy metals, including zinc, aluminum, copper and iron are all toxic to molluscs and are known to be effective molluscicides when used as contact poisons in the form of salts or chelates (Henderson, et al. 1990). Few of them, however, have been successful commercially, perhaps because many such compounds are not palatable to molluscs and are not ingested in sufficient quantities to be effective. More recently, Henderson et al. (UK Patent Application 2 207 866A, 1988) discovered that specific complexes of aluminum with pentanedione compounds and iron with nitroso compounds would act both as ingested and contact poisons.

U.S. Pat. No. 5,437,870 (Puritch et al) discloses an ingestible mollusc poison having a carrier (e.g., a bait), a simple iron compound and a second component. The second component can be ethylene diamine tetracetic acid (EDTA), salts of EDTA, hydroxyethlene triamine diacetic acid, (HEDTA) or salts of HEDTA. Australian Patent Application No. 77420/98 also discloses a stomach-action molluscicide that includes a metal complexone (i.e., iron EDTA) and a carrier.

With the metal-based ingested poisons, the slug must eat and absorb the poison in large enough amounts to reach a lethal threshold. These compounds are much more difficult to formulate and use than are contact poisons, because the compounds are not always palatable to the slug. To be effective, these compounds must be ingested and digested within the mollusc digestive tract in sufficiently high levels to cause a pesticidal effect. However, the activity of Such molluscicides must be slow enough acting to prevent the slug from prematurely becoming sick and to cease feeding on the poison before a lethal dose is ingested. (Henderson and Parker, 1986.) Many of the contact poisons (e.g., aluminum sulfate, copper sulfate, borax, etc.) are useless as ingested poisons because of their deterrence to slugs.

It would thus be desirable to provide a composition that will enhance absorption of stomach-action mollusc poisons without deterring ingestion of the poison by molluscs.

SUMMARY OF THE INVENTION

The invention provides a mollusc stomach poison composition that comprises a simple metal compound, an additive that enhances the activity and absorption of the metal, and a carrier material that is edible to molluscs. The composition is effective to kill molluscs upon being ingested by the mollusc.

The simple metal compound may include metals selected from the group consisting of iron, copper, zinc, aluminum, and mixtures thereof. The term "iron" as used herein is understood to refer to both the ferric and ferrous forms of iron. The activity enhancing additive is a compound selected from the group consisting of ethylene diamine disuccinic acid, isomers of ethylene diamine disuccinic acid, salts of ethylene diamine disuccinic acid, metal complexes of ethylene diamine disuccinic acid and mixtures thereof. The carrier material is one that is edible to molluscs, and it preferably is a mollusc food.

In another embodiment the composition comprises a metal complex of ethylene diamine disuccinic acid or isomers thereof. Metals from which the complex can be formed include iron, copper, zinc, and aluminum.

In another embodiment the mollusc poison composition may also include a co-active ingredient, such as metaldehyde. In yet another embodiment the composition may include or be used with a fertilizer compound, such as a granular fertilizer.

As used herein, the term "mollusc" refers to both terrestrial and aquatic molluscs.

DETAILED DESCRIPTION OF THE INVENTION

The present invention provides a composition that is an ingestible mollusc poison. In one embodiment, the composition includes a simple metal compound, an activity-enhancing additive which is believed to increase the efficacy of the metal compound, and a carrier that is edible to molluscs. Additional formulation enhancing additives may be included as well. Examples of such compounds include pH-adjusting compounds, preservatives, anti-microbial agents, phagostimulants, and taste-altering additives.

The simple metal compound can be one that includes metals such as iron, copper, zinc, aluminum or mixtures thereof. Such a compound may be reduced elemental iron, metal proteins (e.g., iron proteins, copper proteins, zinc proteins, aluminum proteins), metal salts (e.g., iron salts, copper salts, zinc salts, aluminum salts and mixtures thereof), metal carbohydrates (e.g., iron carbohydrates, copper carbohydrates, zinc carbohydrates, aluminum carbohydrates and mixtures thereof). Specific examples of such compounds include iron acetate, iron chloride, iron phosphate, iron phosphate/sodium citrate mixture, sodium iron phosphate, iron pyrophosphate, iron nitrate, iron ammonium sulfate, iron albuminate, iron sulfate, iron sulfide, iron choline citrate, iron glycerol phosphate, iron citrate, iron ammonium citrate, iron fumarate, iron gluconate, iron lactate, iron saccharate, iron fructate, iron dextrate, iron succinate, iron tartrate, copper acetate, copper chloride, copper phosphate, copper pyrophosphate, copper nitrate, copper ammonium sulfate, copper albuminate, copper sulfate, copper gluconate, copper lactate, copper saccharate, copper fructate, copper dextrate, zinc acetate, zinc chloride, zinc phosphate, zinc pyrophosphate, zinc nitrate, zinc ammonium sulfate, zinc albuminate, zinc sulfate, zinc gluconate, zinc lactate, zinc saccharate, zinc fructate, zinc dextrate, aluminum acetate, aluminum chloride, aluminum phosphate, aluminum pyrophosphate, aluminum nitrate, aluminum ammonium sulfate, aluminum albuminate, aluminum sulfate, aluminum gluconate, aluminum lactate, aluminum saccharate, aluminum fructate, and aluminum dextrate. It is understood that the term "iron" as used herein refers to both the ferric and ferrous forms of this element.

As noted above, the activity enhancing additive is one that improves the efficacy of the metal compound by enhancing the digestive absorption of the metal. A preferred activity enhancing additive is ethylene diamine disuccinic acid (EDDS), in both its naturally occurring and synthetic forms. Further, the activity enhancing additive may be in the form of isomers of ethylene diamine disuccinic acid, salts of ethylene diamine disuccinic acid, metal complexes of ethylene diamine disuccinic acid and mixtures thereof.

Activity enhancing additives such as EDDS, its isomers, and its derivatives, are believed to contribute to the rapid absorption of the simple metal compound from the mollusc digestive tract into the internal organs of the animal. This results in rapid, irreversible destruction of the cellular integrity of the mollusc which prevents continuing feeding on plant material, eventually leading to death. EDDS is believed to affect parts of the mollusc digestive system by allowing the metal to be more freely and quickly dispersed throughout the mollusc body. The result of such overload of metal results in pathological distress to the mollusc system.

EDDS is a hexadentate ligand that occurs naturally and which is produced by a number of microorganisms including the actinomycete, Amycolatopsis japonicum sp. nov. (Nishikori et al. J. Antibiot. 37:426–427 (1994); Goodfellow et al, Systematics and Applied Microbiology 20.78–84 (1997). The molecular formula for this compound is $C_{10}H_{16}N_2O_2$ for the acid and $C_{10}H_{13}N_2O_8Na_3$ for the trisodium salt. The acid has a molecular mass of 292.25 while the trisodium salt is 358.19. The compound can occur in three stereoisomers, [R,R], [R,S/S,R], and [S,S]. EDDS can also be synthesized by a reaction of L-aspartic acid and 1,2-dihaloethane, as disclosed in U.S. Pat. No. 5,554,791.

EDDS has been developed commercially as a trisodium salt compound sold under the trademark Octaquest® E-30 by the Associated Octel Company Ltd. This compound has the ability to complex with metals to serve as a chelator. It has the advantage of easily biodegrading and does not persist in the environment (Schowanek et al., Chemosphere 34:2375–2391 (1997)). Hence, it has been proposed for use as a surfactant in laundry detergents as disclosed in U.S. Pat. No. 4,704,233.

Useful salts of ethylene diamine disuccinic acid that may serve as an activity enhancing additive according to the present invention include alkali metal salts, alkali earth salts, ammonium salts and substituted ammonium salts of this compound, as well as mixtures thereof. Preferred salts include the sodium, potassium, and ammonium salts.

The activity enhancing additive may also be in the form of metal complexes of ethylene diamine disuccinic acid. Examples of such complexes include iron EDDS complexes, as well as copper, zinc, and aluminum complexes of EDDS. In one embodiment, the composition may be used without a simple metal compound as a separate component. Instead, the compound can be used in the form of a metal complex of EDDS, with metals selected from iron, copper, zinc, and aluminum.

Suitable carrier materials are those that are edible to molluscs. Mollusc foods are an example of a preferred type of carrier material. Examples of suitable mollusc food carriers include wheat flour, wheat cereal, agar, gelatin, oil cake, pet food wheat, soya, oats, corn, citrus mash, rice, fruits, fish by-products, sugars, coated vegetable seeds, coated cereal seeds, casein, blood meal, bone meal, yeast, fats, beer products, and mixtures thereof. Examples of particularly useful mollusc foods include a bone meal—wheat flour mixture having a ratio of bone meal to wheat flour in the range of 50:50 to 90:10 and one formed from wheat flour and sugar at a ratio of wheat flour to sugar in the range of about 90:10 to 95:5.

Other compounds, as noted above, may be added to the composition as formulation enhancing additives. Such compounds include preservatives or anti-microbial agents, phagostimulants, waterproofing agents, taste altering additives, and pH-adjusting additives.

Exemplary preservatives include Legend MK®, available from Rohm & Hass Company of Philadelphia, Pa. and CA-24, available from Dr. Lehmann and Co. of Memmingen/Allgäu, Germany. Preservatives such as these can normally be mixed with water to form a stock solution to be added to the formulation at a concentration in the range of about 10–750 ppm.

Phagostimulants can be added to the composition to attract molluscs and to induce molluscs to feed upon the composition. A variety of phagostimulants can be used, including sugars, yeast products, and casein. Sugars, such as sucrose, are among the more preferred phagostimulants. These additives are normally incorporated within the composition in a dry form. Typically, they can be added to the composition at about I to 2.5% by weight of the total composition.

Waterproofing agents, which can also act as binders, can be added to the composition to improve the weatherability of the composition. These are typically water insoluble compounds such as waxy materials and other hydrocarbons. Examples of suitable waterproofing agents are paraffin wax, stearate salts, beeswax, and similar compounds. One preferred wax compound is PAROWAX®, available from Conros Corp. of Scarborough, Ontario, Canada. Waterproofing agents can be incorporated into the composition in dry form, at about 5 to 12% by weight of the total composition.

It is also desirable to include within the composition taste altering compounds that render the composition unpalatable to animals, such as humans and pets. Exemplary compositions include those having a bitter taste. One such compound is commercially available as BITREX® from McFarlane Smith Ltd. of Edinburgh, Scotland. These compounds typically are added at a very low concentration. For example, a 0.1% BITREX solution can be added to the composition at about 1 to 2% by weight of the total composition.

Useful pH-affecting additives include calcium carbonate, potassium carbonate, potassium hydroxide, ascorbic acid, tartaric acid, and citric acid. Such additives may be used at a concentration in the range of about 0.2 to 5.0% by wt., and they should be effective to adjust the pH to within a range of about 5 to 9.

The molar ratio of the metal in the simple metal compound to the activity enhancing additive may be in the range of about 1:0.02 to 1:58. More preferably, this ratio is in the range of 1:0.3 to 1:12. Further, the metal in the simple metal compound may be present at a concentration range of about 200 to 20,000 ppm (0.02 to 2.0% by weight) while the activity enhancing additive may be present at a concentration in the range of about 2,000 to 60,000 ppm (0.2 to 6.0% by weight of the composition). One exemplary concentration range is about 0.1 to 0.5% by wt. of the composition for the metal and about 0.8 to 6.0% by wt. for the EDDS component.

Where the composition is used without a simple metal compound, i.e., in the form of a metal complex of EDDS, the metal complex can be present at 5000 to 90,000 ppm (0.5 to 9.0% by wt.).

In one embodiment the composition may also include a co-active molluscicidal agent. One such co-active molluscicidal agent is metaldehyde. Other potential co-active molluscicidal agents include methiocarb, carbaryl, isolan, mexcarbate, niclosamide, trifenmorph, carbofuran, anarcardic acid, and plant-derived saponins. Such co-active ingredients may be added to the composition at a concentration in the range of about 0.2 to 5.0% by wt.

In yet another embodiment the composition may also include a fertilizer, such as virtually any plant fertilizer. Suitable fertilizers typically are granular and an example of one useful fertilizer is Ironite®, available from Ironite Products Company of Scottsdale, Ariz. When present, fertilizers may be used at a concentration in the range of about 0.5 to 10.0% by weight of the composition.

The composition of the invention typically is used in dry form and many of the constituent ingredients of the composition are included in dry form. However, it is often useful to include a sufficient amount of water within the composition to form a dough so that the ingredients can be more easily blended. Water is typically added at a concentration of about 15 to 60% by weight of the total composition. Water, however, typically is driven off by heating and drying the molluscicidal bait before it is used. The composition may also be formulated as a liquid, especially where the composition utilizes a metal complex of EDDS.

As noted above, the composition of the present invention is typically used in a dry, spreadable form such as powders, granules, cubes, or pellets. The composition may be spread on or around areas infested by molluscs as well as in areas in which mollusc infestation is to be prevented. When used to combat aquatic molluscs the composition can simply be added to the environment inhabited by the molluscs.

To prepare the composition, a suitable amount of the simple metal compound and the activity enhancing additive can be blended in dry form, with a dry carrier material. Thereafter, other dry ingredients (such as phagostimulants and waterproofing agents) are blended and mixed with the bait. Next, suitable amounts of liquid additives (such as preservatives, taste altering additives and water) are added to the dry mixture to form a dough. The bait can be covered, such as with a plastic wrap, and heated. One preferred heating technique is by heating in a microwave oven for 30 seconds to 10 minutes. After heating, the dough can be processed in a food grinder to obtain strands of the molluscicidal composition. This material is then dried, at elevated or ambient temperatures, and it can be made into a desired form, such as powder, pellets or granules.

One exemplary molluscicidal composition can be prepared as follows. First, metal compounds, e.g. iron carbohydrate or iron salts, are dry blended into a cereal flour (wheat) at between 1000 to 20,000 ppm metal wt/wt. Dry EDDS, or its sodium salt, is then added to the flour on a molar level to the amount of iron added. This level can vary in the range of a metal: EDDS molar ratio in the range of about 1:0.02 to 1:58 ratio. The EDDS is added to the mixture while continually stirring. Other ingredients can be added to the mixture, such as, anti-microbials (Legend®), waterproofing agents, and phagostimulants (e.g., sugar). Water soluble additives are dissolved in water and then the water is blended into the dry wheat/iron compounds plus EDDS mixture. The dough is thoroughly mixed in a grinding device and extruded in the form of noodles. The resultant bait is dried at 40 degrees Celsius for 24 hours before testing.

The metal complexes can be synthesized by combining virtually any soluble metal compound, such as ferrous sulfate, with soluble EDDS or virtually any soluble derivative of EDDS. Following this combination, the pH can be adjusted (e.g., in the range of about 5 to 9) with a suitable agent such as a concentrated solution of potassium hydroxide. Exemplary metal compounds include reduced elemental iron, metal proteins (e.g., iron proteins, copper proteins, zinc proteins, aluminum proteins), metal salts (e.g., iron salts, copper salts, zinc salts, aluminum salts and mixtures thereof), metal carbohydrates (e.g., iron carbohydrates, copper carbohydrates, zinc carbohydrates, aluminum carbohydrates and mixtures thereof). Specific examples of such compounds include iron acetate, iron chloride, iron phosphate, iron phosphate/sodium citrate mixture, sodium iron phosphate, iron pyrophosphate, iron nitrate, iron ammonium sulfate, iron sulfide, iron albuminate, iron choline citrate, iron glycerol phosphate, iron citrate, iron ammonium citrate, iron fumarate, iron gluconate, iron lactate, iron saccharate, iron fructate, iron dextrate, iron succinate, iron tartrate, copper acetate, copper chloride, copper phosphate, copper pyrophosphate, copper nitrate, copper ammonium sulfate, copper albuminate, copper sulfate, copper gluconate, copper lactate, copper saccharate, copper fructate, copper dextrate, zinc acetate, zinc chloride, zinc phosphate, zinc pyrophosphate, zinc nitrate, zinc ammonium sulfate, zinc albuminate, zinc sulfate, zinc gluconate, zinc lactate, zinc saccharate, zinc fructate, zinc dextrate, aluminum acetate, aluminum chloride, aluminum phosphate, aluminum pyrophosphate, aluminum nitrate, aluminum ammonium sulfate, aluminum albuminate, aluminum sulfate, aluminum gluconate, aluminum lactate, aluminum saccharate, aluminum fructate, and aluminum dextrate.

Exemplary derivatives of EDDS include isomers of ethylene diamine disuccinic acid, salts of ethylene diamine disuccinic acid, including alkali earth, alkali metal, ammonium, substituted ammonium, mixtures of these salts, metal complexes of ethylene diamine disuccinic acid and mixtures thereof.

The following non-limiting examples serve to further illustrate the present invention.

EXAMPLE 1

A tub test was set up with 20 *Deroceras reticulatum* and two lettuce plants per tub with three tubs per iron treatment and two tubs for controls. Compost soil was used to cover the tub bottoms. Slugs were collected from the field and added to the tubs along with 2 grams of bait. Baits of the type noted in the table below were made the day prior to use.

| Code | Bait |
| --- | --- |
| iron p/EDDS | DSA14/79/1 - 2800 ppm iron as iron phosphate plus 10,800 ppm EDDS, 6.0% sugar and balance of wheat flour |
| Control | R4/118/1 - Control bait made with flour and sugar (94:6)* |

*Unless otherwise noted, controls made with flour and sugar contain 94 parts flour and 6 parts sugar.

The tubs were kept in the greenhouse during assessment period. Data was collected at three and seven days after treatment, and the results obtained are shown below in Tables 1 and 2.

TABLE 1

Observations on mortality at 3 DAT*

| Treat. | REP1 | REP2 | REP3 |
| --- | --- | --- | --- |
| iron p/EDDS | 7/20, bait readily eaten, very light plant feeding | 6/20, 1 missing, bait readily eaten; very light plant feeding | 7/20, bait readily eaten; no plant feeding |
| Control | 0/20, light plant feeding | 1/20, light plant feeding | na |

*DAT = Days After Treatment

TABLE 2

Observations on mortality at 7 DAT.

| Treat. | REP1 | REP2 | REP3 | Total % Kill |
| --- | --- | --- | --- | --- |
| iron p/EDDS | 9/13, no more plant feeding | 8/14 no more plant feeding | 9/13 no more plant feeding | 46/60, 76.7% |
| Control | 2/20, heavy plant feeding | 1/19, heavy plant feeding | na | 4/40, 10.0% |

EXAMPLE 2

A tub test was set up with 15 *Deroceras reticulatum* and two lettuce plant per tub with two tubs per treatment. Compost soil was used to cover the tub bottoms. Slugs were collected from the field and added to the tubs along with 2 grams of bait. Iron EDDS was synthesized from EDDS and iron chloride. Baits of the type noted in the table below were made the day prior to use.

| Code | Bait |
| --- | --- |
| iron EDDS 2000 | R4/122/1 - 2000 ppm iron as iron EDDS, 6.0% sugar and balance of wheat flour |
| iron EDDS 2400 | R4/122/2 - with 2400 ppm iron as iron EDDS, 6.0% sugar and balance of wheat flour |
| iron EDDS 2800 | R4/122/3 with 2800 ppm iron as iron EDDS, 6.0% sugar and balance of wheat flour |
| Control | R4/118/1 - Control bait made with flour and sugar |

The tubs were kept in the greenhouse during assessment period. Data was collected at three and six days after treatment, and the results obtained are shown below in Tables 3 and 4.

TABLE 3

Observations on mortality at 4 DAT

| Treat. | REP1 | REP2 |
| --- | --- | --- |
| iron EDDS 2000 | 3/15, slight plant feeding | 3/15, slight plant feeding |
| iron EDDS 2400 | 4/15, no plant feeding | 11/15, no plant feeding |
| iron EDDS 2800 | 9/15, no plant feeding | 6/15, slight plant feeding |
| Control | 0/15 | 0/15 |

TABLE 4

Observations on mortality at 6 DAT

| Treat. | REP1 | REP2 | Total % Kill |
| --- | --- | --- | --- |
| iron EDDS 2000 | 4/12 | 0/12 | 10/30, 33.3% |
| iron EDDS 2400 | 1/11 | 2/4 | 18/30, 60.0% |
| iron EDDS 2800 | 0/6 | 4/9 | 19/30, 63.3% |
| Control | 0/15 | 0/15 | 0/30, 0% |

EXAMPLE 3

A tub test was set up with 15 *Deroceras reticulatum,* two lettuce plant per tub and two tubs per treatment, except for the aluminum nitrate treatment which had one replicate of 22 slugs. Compost soil was used to cover the tub bottoms. Slugs were collected from the field and added to the tubs along with 2 grams of bait. Tubs were kept outside during the duration of the experiment. Baits of the type noted in the table below were made the day prior to use.

| Code | Bait |
| --- | --- |
| 10A | R4/123/1 - 2800 ppm Cu as Cu acetate and 10,800 ppm EDDS, 6.0% sugar and balance of wheat flour |
| 10B | R4/123/2 - 2800 ppm Cu as Cu chloride and 10,800 ppm EDDS, 6.0% sugar and balance of wheat flour |
| 10C | R4/123/3 - with 2800 ppm Cu as Cu oxide and 10,800 ppm EDDS, 6.0% sugar and balance of wheat flour |
| 10D | R4/123/6 - 2800 ppm Zn as Zinc chloride and 10,800 ppm EDDS, 6.0% sugar and balance of wheat flour |
| 10E | R4/122/3 - with 2800 ppm iron as iron phosphate and 10,800 ppm EDDS |
| 10F | R4/118/1 - Control bait made with flour and sugar |
| 10G | R4/123/5 - with 2800 ppm Al as Al nitrate and 10,800 ppm EDDS, 6.0% sugar and balance of wheat flour |

The tubs were kept in the greenhouse during assessment period. Data was collected at three and seven days after treatment, and the results obtained are shown below in Tables 5 and 6.6.

TABLE 5

Observations on mortality at 3 DAT

| Treat. | REP1 | REP2 |
|---|---|---|
| 10A | 0/15, no plant feeding | 2/15, no plant feeding |
| 10B | 0/15, both plants eaten | 2/15, 1 plant eaten |
| 10C | 1/15, medium plant feeding | 1/15, light plant feeding |
| 10D | 2/15, light plant feeding | 2/15, light plant feeding |
| 10E | 7/15, no plant feeding | 5/17, no plant feeding |
| 10F | 1/15 | 0/15 |
| 10G | 0/22, both plants eaten | na |

TABLE 6

Observations on mortality at 7 DAT

| Treat. | REP1 | REP2 | Total % Kill |
|---|---|---|---|
| 10A | 3/15 | 3/11* | 8/28, 28.6% |
| 10B | 0/15 | 1/13 | 3/30, 10.0% |
| 10C | 0/14 | 2/14 | 4/30, 13.3% |
| 10D | 3/13 | 1/13 | 8/30, 28.6% |
| 10E | 7/8 | 10/12 | 29/32, 90.1% |
| 10F | 0/14 | 1/15 | 2/30. 6.6% |
| 10G | 4/22 | na | 4/22, 18.2% |

*= 2 slugs missing

EXAMPLE 4

A test tub was set up with two replicates per treatment of 10 *Arion ater*. Two lettuce plants were placed per tub. Compost soil was used to cover the tub bottoms. Slugs were collected from the field and added to the tubs along with 5 grams of bait. Tubs were kept outside during the experimental period. The baits were made by dissolving the sodium EDDS and iron sugar in water, adding the flour and then adjusting the pH with $K_2CO3$. Tubs were kept outside during the duration of the experiment. Baits of the type noted in the table below were made the day prior to use.

| | |
|---|---|
| 8A | R4/139/1, 0.28% iron (iron sugar) + 1.08% NaEDDS, pH 7.33 |
| 8B | R4/139/2, 0.28% iron (iron sugar) + 1.08% NaEDDS, pH 8.45 |
| 8C | R4/139/3, 0.28% iron (iron sugar) + 1.08% NaEDDS, pH 9.53 |
| 8D | R4/139/4, 0.28% iron (iron sugar) + 1.08% NaEDDS, pH 10.5 |
| 8E | R4/139/5, 0.28% iron (iron sugar) + 1.08% NaEDDS, not premixed |
| 8F | DSA/120/1, Control bait made with flour and sugar |

The tubs were kept outside during the assessment period. Data was collected at four and six days after treatment, and the results obtained are shown below in Tables 7 and 8.

TABLE 7

Observations on mortality at 4 DAT

| Treat. | REP1 | REP2 |
|---|---|---|
| 8A | 0/10, bait 55% gone, no plant feeding | 1/10, bait 100% gone, no plant feeding |
| 8B | 0/10, bait 100% gone, no plant feeding | 0/10, bait 100% gone, medium plant feeding |
| 8C | 0/10, bait 70% gone, heavy plant feeding | 0/10, bait 100% gone, heavy plant feeding |
| 8D | 0/10, bait 5.0% gone, heavy plant feeding | 0/10, bait 5% gone, medium plant feeding |

TABLE 7-continued

Observations on mortality at 4 DAT

| Treat. | REP1 | REP2 |
|---|---|---|
| 8E | 1/10, bait 100% gone, light plant feeding | 0/10, bait 100% gone, medium plant feeding |
| 8F | 0/10 | 0/10 |

TABLE 8

Observations on mortality 6 DAT.

| Treat. | REP 1 | REP2 | Total % Kill |
|---|---|---|---|
| 8A | 7/10 | 5/9 | 13/20, 65.0% |
| 8B | 8/10 | 5/10 | 13/20, 65.0% |
| 8C | 8/10 | 5/10 | 13/20, 65.0% |
| 8D | 0/10 | 1/10 | 1/20, 5.0% |
| 8E | 6/9 | 6/10 | 13/20, 65.0% |
| 8F | 0/10 | 0/10 | 0/20, 0.0% |

EXAMPLE 5

A test tub was set up with two replicates per treatment of 10 *Arion ater*. One large cabbage plant was placed per tub. Compost soil was used to cover the tub bottoms. Slugs were collected from the field and added to the tubs along with 5 grams of bait. Tubs were kept outside during the experimental period. Baits of the type noted in the table below were made the day prior to use.

| | |
|---|---|
| 7A | R4/138/4, 2800 ppm iron as iron phosphate + 1.08% EDDS |
| 7B | R4/140/1, 2800 ppm iron as iron phosphate + 2.5% EDDS |
| 7C | R4/138/1, 4000 ppm iron as iron phosphate + 2.5% EDDS |
| 7D | R4/138/2, 4500 ppm iron as iron phosphate + 2.5% EDDS |
| 7E | DSA/120/1, Control bait made with flour and sugar |

The tubs were kept outside during the assessment period. Data was collected at four and seven days after treatment, and the results obtained are shown below in Tables 9 and 10.

TABLE 9

Observations on mortality at 4 DAT

| Treat. | REP1 | REP2 |
|---|---|---|
| 7A | 2/10, no plant feeding, most bait gone | 3/10, med plant feeding, lots bait left |
| 7B | 5/10, no plant feeding, most bait gone | 5/10, light plant feeding, most bait gone |
| 7C | 5/10, heavy plant feeding, lots bait left | 8/10, heavy plant feeding, some bait left |
| 7D | 7/10, no plant feeding, lots bait left | 6/10, no plant feeding, lots bait left |
| 7E | 0/10 | 0/10 |

TABLE 10

Observations on mortality at 7 DAT

| Treat. | REP 1 | REP2 | Total % Kill |
|---|---|---|---|
| 7A | 7/8 | 4/7 | 16/20, 80.0% |
| 7B | 3/5 | 3/5 | 16/20, 80.0% |
| 7C | 3/5 | 1/2 | 17/20, 85.0% |

TABLE 10-continued

| | Observations on mortality at 7 DAT | | |
|---|---|---|---|
| Treat. | REP 1 | REP2 | Total % Kill |
| 7D | 3/3 | 1/4 | 17/20, 85.0% |
| 7E | 0/10 | 0/10 | 0/20, 0.0% |

EXAMPLE 6

A standard tub test was set up with 15 *Deroceras reticulatum* and one lettuce plant per tub and two tubs per treatment. Compost soil was used to cover the tub bottoms. Slugs were collected from the field and added to the tubs along with 2 grams of bait. Tubs were kept outside during the experimental period. Baits of the type noted in the table below were made the day prior to use.

| Code | Bait |
|---|---|
| 6A | R4/155/1, 0.28% iron as iron phospahate and 1.50% EDDS |
| 6B | R4/155/2, 0.28% iron as iron phospahate and 1.75% EDDS |
| 6C | R4/153/1, 0.28% iron as iron phospahate and 2.25% EDDS |
| 6D | R4/155/3, 0.28% iron as iron phospahate and 2.75% EDDS |
| 6E | R4/140/2, 0.28% iron as iron phospahate and 3.00% EDDS |
| 6F | R4/120/1 Control bait made with flour and sugar |

Data was collected at four and seven days after treatment, and the results obtained are shown below in Tables 11 and 12.

TABLE 11

| | Observations on mortality at 4 DAT | |
|---|---|---|
| Treat. | REP1 | REP2 |
| 6A | 2/15 | 1/15 |
| 6B | 4/15 | 4/15 |
| 6C | 2/15 | 0/15 |
| 6D | 2/15 | 1/15 |
| 6E | 1/15 | 1/15 |
| 6F | 0/15 | 0/16 |

TABLE 12

| | Observations on mortality at 7 DAT | | |
|---|---|---|---|
| Treat. | REP1 | REP2 | Total % Kill |
| 6A | 4/13 | 4/14 | 11/30, 36.7% |
| 6B | 2/11 | 9/11 | 19/30, 63.3% |
| 6C | 5/13 | 7/15 | 14/30, 46.7% |
| 6D | 7/13 | 3/14 | 13/30, 43.3% |
| 6E | 5/14 | 3/14 | 10/30, 33.3% |
| 6F | 1/15 | 0/16 | 1/31, 3.3% |

EXAMPLE 7

A standard tub test was set up with 15 *Deroceras reticulatum* and one lettuce plant per tub and two tubs per treatment. Compost soil was used to cover the tub bottoms. Slugs were collected from the field and added to the tubs along with 2 grams of bait. Tubs were kept outside during the experimental period. Baits of the type noted in the table below were made the day prior to use.

| Code | Bait |
|---|---|
| 5A | R4/154/1, iron phosphate/EDDS in a 50:50 bait of bonemeal: flour |
| 5B | R4/154/2, iron phosphate/EDDS in a 90:10 bait of bonemeal: flour |
| 5C | R4/143/3 Control bait made with flour and sugar |

Data was collected at four and seven days after treatment, and the results obtained are shown below in Tables 13 and 14.

TABLE 13

| | Observations on mortality at 4 DAT | |
|---|---|---|
| Treat. | REP1 | REP2 |
| 5A | 6/15 | 3/15 |
| 5B | 2/15 | 4/14** |
| 5C | 0/15 | 0/15 |

** = 1 missing slug

TABLE 14

| | Observations on mortality at 7 DAT | | |
|---|---|---|---|
| Treat. | REP1 | REP2 | Total % Kill |
| 5A | 7/9 | 8/12 | 24/30, 80.0% |
| 5B | 5/13 | 7/10 | 18/29, 62.1% |
| 5C | 0/15 | 0/15 | 0/30, 0.0% |

EXAMPLE 8

A standard tub test was set up with 15 *Deroceras reticulatum* and one lettuce plant per tub and two tubs per treatment. Compost soil was used to cover the tub bottoms. Slugs were collected from the field and added to the tubs along with 2 grams of bait. Tubs were kept outside during the experimental period. Baits of the type noted in the table below were made the day prior to use.

| Code | Bait |
|---|---|
| 4A | R4/159/1, 0.28% iron as iron sugar with 2.25% EDDS |
| 4B | R4/159/2, 0.28% iron as iron gluconate with 2.25% EDDS |
| 4C | R4/159/3, iron phosphate plus 2.25% EDDS plus 0.5% sodium gluconate |
| 4D | R4/159/4, iron phosphate plus 2.25% EDDS plus 0.5% calcium citrate |
| 4E | R4/153/1, iron phosphate plus 2.25% EDDS |
| 4F | R4/143/3 Control bait made with flour and sugar |

Data was collected at four and seven days after treatment, and the results obtained are shown below in Tables 15 and 16.

TABLE 15

| | Observations on mortality at 4 DAT | |
|---|---|---|
| Treat. | REP1 | REP2 |
| 4A | 8/15 | 5/15 |
| 4B | 2/15 | 2/15 |
| 4C | 1/15 | 1/15 |
| 4D | 0/15 | 1/15 |

TABLE 15-continued

Observations on mortality at 4 DAT

| Treat. | REP1 | REP2 |
|---|---|---|
| 4E | 5/15 | 2/15 |
| 4F | 0/15 | 0/15 |

TABLE 16

Observations on mortality at 7 DAT

| Treat. | REP1 | REP2 | Total % Kill |
|---|---|---|---|
| 4A | 4/7 | 5/10 | 23/30, 76.7% |
| 4B | 5/13 | 9/13 | 18/30, 60.0% |
| 4C | 1/14 | 3/13, 1 missing | 6/29, 20.7% |
| 4D | 6/15 | 4/14 | 11/30, 36.7% |
| 4E | 3/10 | na | 7/15, 46.7% |
| 4F | 0/15 | 0/15 | 0/30, 0.0% |

EXAMPLE 9

A standard tub test was set up with 10 *Arion ater* and one lettuce plant per tub and two tubs per treatment. Compost soil was used to cover the tub bottoms. Slugs were collected from the field and added to the tubs along with 6 grams of bait and two cabbage plants. Tubs were kept outside during the experimental period. Baits of the type noted in the table below were made the day prior to use.

| Code | Bait |
|---|---|
| 3A | R4/161/1, 0.28% iron as iron sugar with 2.25% EDDS |
| 3B | R4/161/6, 0.28% iron as iron sulfate with 2.25% EDDS |
| 3C | R4/161/4, 0.28% iron as iron EDDS made from iron lactate |
| 3D | R4/156/1, 0.28% iron as iron EDDS made from iron sulfate |
| 3E | R4/143/3 Control bait made with flour and sugar |

Data was collected at six days after treatment, and the results obtained are shown below in Table 17.

TABLE 17

Observations on mortality at 6 DAT

| Treat. | REP1 | REP2 | Total % Kill |
|---|---|---|---|
| 3A | 10/10, no plant feeding | 7/10, very light plant feeding | 17/20, 85.0% |
| 3B | 9/10, very light plant feeding | 6/10, light plant feeding | 15/20, 75.0% |
| 3C | 3/10, no plant feeding | 3/10, no plant feeding | 6/20, 30.0% |
| 3D | 4/10, no plant feeding | 1/10, no plant feeding | 5/20, 25.0% |
| 3E | 0/10 | 0/10 | 0/20, 0.0% |

EXAMPLE 10

A standard tub test was set up with 15 *Deroceras reticulatum* and two lettuce plants per tub and two tubs per treatment. Compost soil was used to cover the tub bottoms. Slugs were collected from the field and added to the tubs along with 2 grams of bait. Tubs were kept outside during the experimental period. Baits of the type noted in the table below were made the day prior to use.

| Code | Bait |
|---|---|
| 2A | R4/164/2, 0.28% iron as iron sulfate with 2.25% EDDS at pH 3.58 |
| 2B | R4/167/1, 0.28% iron as iron sulfate with 2.25% EDDS at pH 5.54 |
| 2C | R4/167/2, 0.28% iron as iron sulfate with 2.25% EDDS at pH 7.34 |
| 2D | R4/167/3, 0.28% iron as iron sulfate with 2.25% EDDS at pH 9.30 |
| 2E | R4/167/4, 0.28% iron as iron sulfate with 2.25% EDDS at pH 9.78 |
| 2F | R4/162/2, 0.28% iron as iron phosphate with 2.25% EDDS |
| 2G | R4/162/1 Control bait made with flour and sugar |

Data was collected at four and seven days after treatment, and the results obtained are shown below in Tables 18 and 19.

TABLE 18

Observations on mortality at 4 DAT

| Treat. | REP1 | REP2 |
|---|---|---|
| 2A | 6/16, no plant feeding | 6/16, no plant feeding |
| 2B | 5/15, no plant feeding | 7/15, no plant feeding |
| 2C | 5/15, no plant feeding | 6/15, no plant feeding |
| 2D | 5/15, no plant feeding | 4/15, no plant feeding |
| 2E | 2/15, no plant feeding | 1/15, no plant feeding |
| 2F | 1/15, no plant feeding | 2/15, light plant feeding |
| 2G | 0/15 | 0/15 |

TABLE 19

Observations on mortality at 7 DAT

| Treat. | REP1 | REP2 | Total % Kill |
|---|---|---|---|
| 2A | 6/10 | 8/10 | 26/30, 86.7% |
| 2B | 7/10 | 7/8 | 26/30, 86.7% |
| 2C | 8/10 | 7/9 | 26/30, 86.7% |
| 2D | 4/10 | 7/11 | 20/30, 66.7% |
| 2E | 5/13 | 7/14 | 15/30, 50.0% |
| 2F | 7/14 | 8/13 | 18/30, 60.0% |
| 2G | 0/15 | 0/15 | 0/30, 0.0% |

EXAMPLE 11

A standard tub test was set up with 15 *Deroceras reticulatum* and one lettuce and one cabbage plant per tub and two tubs per treatment. Compost soil was used to cover the tub bottoms. Slugs were collected from the field and added to the tubs along with 2 grams of bait. Tubs were kept in a outside during the experimental period. Baits of the type noted in the table below were made the day prior to use.

| Code | Bait |
|---|---|
| 1A | R4/170/1, 0.28% iron as Fe II sulfate with 2.25% EDDS |
| 1B | R4/170/2, 0.15% iron as Fe II sulfate with 2.25% EDDS |
| 1C | R4/164/2, 0.28% iron as Fe III sulfate with 2.25% EDDS |
| 1D | R4/170/3, 0.28% iron as iron sugar (10%) with 2.5% EDDS |
| 1E | R4/161/1, 0.28% iron as iron sugar (20%) with 2.5% EDDS |
| 1F | R4/162/2, 0.28% iron as Fe III phosphate with 2.25% EDDS |
| 1G | R4/162/1 Control bait made with flour and sugar |

Data was collected at four and seven days after treatment, and the results obtained are shown below in Tables 20 and 21.

TABLE 20

Observations on mortality and plant feeding at 4 DAT

| Treat. | REP1 | REP2 |
|---|---|---|
| 1A | 3/15, no plant feeding | 3/15, no plant feeding |
| 1B | 2/15, no plant feeding | 3/15, no plant feeding |
| 1C | 3/15, no plant feeding | 1/15, no plant feeding |
| 1D | 3/15, no plant feeding | 5/15, no plant feeding |
| 1E | 5/15, no plant feeding | 4/15, no plant feeding |
| 1F | 2/15, no plant feeding | 1/15, no plant feeding |
| 1G | 0/15 | 0/15 |

TABLE 21

Observations on mortality at 7 DAT

| Treat. | REP1 | REP2 | Total % Kill |
|---|---|---|---|
| 1A | 9/12 | 7/12 | 22/30, 73.3% |
| 1B | 9/13 | 7/12 | 21/30, 70.0% |
| 1C | 10/12 | 11/14 | 25/30, 83.3% |
| 1D | 11/12 | 8/10 | 27/30, 90.0% |
| 1F | 8/10 | 6/11 | 23/30, 76.7% |
| 1F | 6/13 | 5/14 | 14/30, 46.7% |
| 1G | 0/15 | 1/15 | 1/30, 3.3% |

Having described the preferred embodiments of the invention, it will be apparent to one of ordinary skill in the art that other embodiments incorporating their concepts may be used. It is believed, therefore, that these embodiments should not be limited to disclosed embodiments but rather should be limited only by the spirit and scope of the appended claims. All publications and references cited herein are expressly incorporated herein by reference in their entirety. Unless otherwise noted, all percentages by weight are percent of the total composition.

What is claimed is:

1. A mollusc stomach poison composition, comprising:
   a simple metal compound, including metals selected from the group consisting of iron, copper, zinc, aluminum and mixtures thereof;
   an activity enhancing additive selected from the group consisting of ethylene diamine disuccinic acid, isomers of ethylene diamine disuccinic acid, salts of ethylene diamine disuccinic acid, metal complexes of ethylene diamine disuccinic acid and mixtures thereof; and
   a carrier material edible to molluscs, the mollusc stomach poison being effective to kill molluscs upon ingestion by molluscs.

2. The composition of claim 1, wherein the salt of ethylene diamine disuccinic acid is selected from the group consisting essentially of alkali metal salts, alkali earth salts, ammonium salts, substituted ammonium salts, and mixtures thereof.

3. The composition of claim 1, further comprising a molluscicidal co-active ingredient.

4. The composition of claim 3, wherein the molluscicidal co-active ingredient is selected from the group consisting of metaldehyde, methiocarb, carbaryl, isolan, mexcarbate, mercaptodimethur, niclosamide, trifenmorph, carbofuran, anarcardic acid, plant-derived saponins, and mixtures thereof.

5. The composition of claim 1, further comprising a pH-adjusting agent.

6. The composition of claim 5, wherein the pH-adjusting agent is selected from the group consisting of calcium carbonate, potassium carbonate, potassium hydroxide, ascorbic acid, tartaric acid, and citric acid.

7. The composition of claim 5, wherein the pH-adjusting agent results in the composition having a pH in the range of about 5 to 9 when measured as a dough during preparation of the mollusc stomach poison composition prior to a drying phase of the composition.

8. The composition of claim 1, wherein the molar ratio of the metal to the bait additive is in the range of about 1:0.02 to 1:58.

9. The composition of claim 1, wherein the metal is present in the simple metal compound at a concentration in the range of about 200 to 20,000 ppm.

10. The composition of claim 1, wherein the activity enhancing additive is present at a concentration in the range of about 0.2 to 6.0 percent by wt. of the composition.

11. The composition of claim 1, wherein the carrier is a mollusc food.

12. The composition of claim 11, wherein the mollusc food is selected from the group consisting of wheat flour, wheat cereal, agar, gelatin, oil cake, pet food wheat, soya, oats, corn, citrus mash, rice, fruits, fish by-products, sugars, coated vegetable seeds, coated cereal seeds, casein, blood meal, bone meal, yeast, fats, beer products, and mixtures thereof.

13. The composition of claim 11, wherein the mollusc food is a bone meal—wheat flour mixture having a ratio of bone meal to wheat flour in the range of 50:50 to 90:10.

14. The composition of claim 1, wherein the simple metal compound is selected from the group consisting of reduced elemental iron, iron proteins, iron salts, iron carbohydrates, copper proteins, copper salts, copper carbohydrates, zinc proteins, zinc salts, zinc carbohydrates, aluminum proteins, aluminum salts, aluminum carbohydrates, and mixtures thereof.

15. The composition of claim 14, wherein the simple metal compound is selected from the group consisting of iron acetate, iron chloride, iron phosphate, iron phosphate/sodium citrate mixture, sodium iron phosphate, iron pyrophosphate, iron nitrate, iron ammonium sulfate, iron albuminate, iron sulfate, iron sulfide, iron choline citrate, iron glycerol phosphate, iron citrate, iron ammonium citrate, iron fumarate, iron gluconate, iron lactate, iron saccharate, iron fructate, iron dextrate, iron succinate, iron tartrate, copper acetate, copper chloride, copper phosphate, copper pyrophosphate, copper nitrate, copper ammonium sulfate, copper albuminate, copper sulfate, copper gluconate, copper lactate, copper saccharate, copper fructate, copper dextrate, zinc acetate, zinc chloride, zinc phosphate, zinc pyrophosphate, zinc nitrate, zinc ammonium sulfate, zinc albuminate, zinc sulfate, zinc gluconate, zinc lactate, zinc saccharate, zinc fructate, zinc dextrate, aluminum acetate, aluminum chloride, aluminum phosphate, aluminum pyrophosphate, aluminum nitrate, aluminum ammonium sulfate, aluminum albuminate, aluminum sulfate, aluminum gluconate, aluminum lactate, aluminum saccharate, aluminum fructate, and aluminum dextrate.

16. A method of exterminating unwanted mollusc pests, comprising the steps of:
   providing a molluscicidal composition including
      a simple metal compound, including metals selected from the group consisting of iron, copper, zinc or aluminum and mixtures thereof, an activity enhancing additive selected from the group consisting of ethylene diamine disuccinic acid, isomers of ethylene diamine disuccinic
      acid, salts of ethylene diamine disuccinic acid, metal complexes of ethylene diamine disuccinic acid and mixtures thereof, and a carrier material edible to molluscs;

applying the molluscicidal composition to an area infested with molluscs; and allowing the molluscs to ingest the molluscicidal composition.

17. A method of exterminating unwanted mollusc pests, comprising the steps of:

providing a molluscicdal composition including
a metal compound selected from the group consisting of ferric ethylene diamine disuccinic acid, ferrous ethylene diamine disuccinic acid, copper ethylene diamine disuccinic acid, zinc ethylene diamine disuccinic acid, aluminum ethylene diamine disuccinic acid, and mixtures thereof, and
a carrier material edible to molluscs;

applying the molluscicidal composition to an area infested with molluscs; and allowing the molluscs to ingest the molluscicidal composition.

18. An ingestible molluscicidal composition, comprising:

a metal compound selected from the group consisting of ferric ethylene diamine disuccinic acid, ferrous ethylene disuccinic acid, copper ethylene diamine disuccinic acid, zinc ethylene diamine disuccinic acid, aluminum ethylene diamine disuccinic acid, and mixtures thereof; and a carrier material edible to molluscs.

19. The composition of claim 18, wherein the carrier material is a mollusc food.

20. The composition of claim 18, further comprising a co-active molluscicidal agent.

21. The composition of claim 20, wherein the co-active molluscicidal agent is selected from the group consisting of metaldehyde, methiocarb, carbaryl, isolan, mexcarbate, mercaptodimethur, niclosamide, trifenmorph, carbofuran, anarcardic acid, plant-derived saponins, and mixtures thereof.

22. The composition of claim 18, wherein the metal is present in the metal compound at a concentration in the range of about 0.5 to 9.0 percent by wt. of the composition.

* * * * *